(12) United States Patent
Fujimoto (10) Patent No.: US 10,137,036 B2
(45) Date of Patent: Nov. 27, 2018

(54) UNDERWATER MASK

(71) Applicant: TABATA CO., LTD., Tokyo (JP)

(72) Inventor: Takashi Fujimoto, Tokyo (JP)

(73) Assignee: TABATA CO., LTD., Tokyo (JP)

( * ) Notice: Subject to any disclaimer, the term of this patent is extended or adjusted under 35 U.S.C. 154(b) by 362 days.

(21) Appl. No.: 14/898,814

(22) PCT Filed: Jun. 20, 2014

(86) PCT No.: PCT/JP2014/066483
§ 371 (c)(1),
(2) Date: Dec. 16, 2015

(87) PCT Pub. No.: WO2014/204004
PCT Pub. Date: Dec. 24, 2014

(65) Prior Publication Data
US 2016/0120701 A1 May 5, 2016

(30) Foreign Application Priority Data
Jun. 21, 2013 (JP) .................... 2013-131159

(51) Int. Cl.
*A61F 9/02* (2006.01)
*A63B 33/00* (2006.01)
*B63C 11/12* (2006.01)

(52) U.S. Cl.
CPC ............ *A61F 9/027* (2013.01); *A63B 33/002* (2013.01); *B63C 11/12* (2013.01); *B63C 2011/128* (2013.01)

(58) Field of Classification Search
CPC .......... A61F 9/027; A61F 9/025; A61F 9/029; A63B 33/002; A63B 33/00;
(Continued)

(56) References Cited

U.S. PATENT DOCUMENTS 6,131,246 A 10/2000 Paulson et al.
6,350,030 B2 * 2/2002 Fujima .................... A61F 9/027
2/426
(Continued)

FOREIGN PATENT DOCUMENTS

JP 09132193 A * 5/1997 ............. B63C 11/12
JP 2001037911 A * 2/2001 .......... A63B 33/002
(Continued)

*Primary Examiner* — Anna Kinsaul
*Assistant Examiner* — Griffin Hall
(74) *Attorney, Agent, or Firm* — Clark & Brody (57) ABSTRACT

An underwater mask includes a buckle with a strap that can be moved and adjusted in the up-down and lateral directions on a wearer's head. The buckle includes a base including a spring with a locking hook, a strap adjuster body turnably attached to the base and including a plurality of engaging teeth configured to sequentially engage with the locking hook according to the turn, a handling member held inside the body and operated from outside the body, and a stopper held by the body. The handling member includes a spring, sliding portion, and a pair of finger pads exposed outside the body by the spring. The stopper includes a sliding contact tapered protrusion that slides sliding against the pair of sliding portions to cause the stopper to swing toward a direction opposite to the strap adjuster body and release the pawl from the engaging teeth of the strap.

8 Claims, 11 Drawing Sheets

(58) Field of Classification Search
CPC ........ A63B 2033/004; A63B 2033/006; A63B 2033/008; B63C 11/12; B63C 2011/128; A44B 11/12; Y10T 24/4016; Y10T 24/4072; Y10T 24/1371; Y10T 24/4736
USPC ... 2/426, 428, 439, 452, 453, 425, 427, 440, 2/442, 445, 446, 448, 450
See application file for complete search history.

(56) References Cited

U.S. PATENT DOCUMENTS

| | | | |
|---|---|---|---|
| 6,477,717 B1 * | 11/2002 | Winefordner | B63C 11/12 2/428 |
| 6,748,608 B1 * | 6/2004 | Fukazawa | A63B 33/002 2/428 |
| 7,003,811 B2 * | 2/2006 | Canavan | A61F 9/027 2/448 |
| 7,134,149 B2 * | 11/2006 | Sato | B63C 11/12 2/431 |
| 9,241,542 B2 * | 1/2016 | Kuo | A44B 11/006 |
| 2004/0078874 A1 | 4/2004 | Sato | |
| 2007/0028371 A1 | 2/2007 | Chiang | |
| 2012/0160989 A1 | 6/2012 | Yasuhara et al. | |

FOREIGN PATENT DOCUMENTS

| | | | | |
|---|---|---|---|---|
| JP | 2001218869 A | * | 8/2001 | ............ A61F 9/027 |
| JP | 2004-136057 | | 5/2004 | |
| JP | 2012-139360 | | 7/2012 | |

* cited by examiner

UNDERWATER MASK

TECHNICAL FIELD

The present invention relates to an underwater mask including buckle configured to couple a strap to a mask body.

BACKGROUND

An underwater mask disclosed in Patent Literature 1 includes mask body including a lens, a lens frame, and a skirt that extends rearward from the lens frame, buckle on both sides of the lens frame, and a strap length-adjustably wound through the buckle. The buckle includes turning angle adjusting means for adjusting the position of the strap, and adjuster unit used for adjusting the length of the strap.

CITATION LIST

Patent Literature

{PTL 1} JP 2004-136057 A

SUMMARY

Technical Problem

In the underwater mask in Patent Literature 1, use of the turning angle adjusting means of the buckle can adjust the position of the strap vertically and dispose the strap in a desired position. The length of the strap can be adjusted using the adjuster unit to fit the size of wearers' heads. This adjustment, however, takes some effort because the adjustment requires the procedure of releasing the locks of strap adjusters, adjusting the length appropriately, and locking the strap on the adjusters again to be done with both hands. In addition, with the adjuster unit, the face fit of the mask bodies can be adjusted with the strap, but the underwater mask cannot be laterally adjusted in accordance with the size of wearers' face, which results in difficulty in sufficiently fitting the strap to the outlines of wearers' head.

The present invention has an object to provide an improvement in the conventional underwater mask, in other words, to provide an underwater mask including buckle with which a strap can be moved in vertical direction and lateral directions on a wearer' s head by relatively easy handling.

Solution to Problem

To achieve the object above, the present invention is directed to an improvement of an underwater mask having an up-down direction and a lateral direction, the underwater mask including a mask body and a strap. The mask body includes a lens frame and a skirt extending rearward from the lens frame. The lens frame includes a lens on the front. The strap is configured to be coupled to at least one side of both sides of the mask body through a buckle. The strap includes a plurality of engaging teeth.

In the underwater mask according to the present invention, the buckle includes a base, a strap adjuster body, a handling member, and a stopper. The base includes a second coupling portion, a circular fitting hole, and a spring. The second coupling portion is configured to be coupled to a first coupling portion on the at least one side turnably in the lateral direction. The spring includes a locking hook. The strap adjuster body includes a plurality of engaging teeth, a cylindrical fitting shaft, a guide shaft, a slide guide groove hole, and a pair of guide openings. The engaging teeth face the spring and are capable of sequentially engaging with the locking hook. The cylindrical fitting shaft is configured to be fitted into the circular fitting hole turnably by a predetermined angle in the circumferential direction of the cylindrical fitting shaft. The guide shaft is configured to be wound by the strap. The slide guide groove hole extends in the up-down direction. The pair of guide openings face each other in the up-down direction. The handling member includes an approximately V-shaped spring, a slider, a pair of sliding unit near the slider, and a pair of finger pads outside the pair of sliding unit. The slider is capable of sliding along the slide guide groove hole. The finger pads are configured to be exposed from the guide openings of the strap adjuster body. The stopper includes a pawl and a sliding contact tapered protrusion near the pawl. The pawl is capable of sequentially engaging with the engaging teeth of the strap. The sliding contact tapered protrusion is slidably disposed between the pair of sliding unit. The stopper is configured to be held by the strap adjuster body swingably toward a direction opposite to the body.

Advantageous Effects of Invention

An underwater mask according to equal to or more than one embodiment of the present invention includes a turning mechanism for a buckle to rotate in the lateral direction of a mask body and a turning angle adjusting mechanism holding a strap adjuster body turnably with respect to a base by a predetermined angle, so that a strap can move in the up-down direction and the lateral direction on a wearer's head. Thus, the strap can be moved to suit the size or other conditions of the wearer's head in the up-down direction and the lateral direction, and an appropriate feeling of how a skirt touches the skin of the wearer's face and an appropriate position of the strap in the up-down direction and the lateral direction can be retained. This movement and retention can cause the underwater mask to fit the wearer's face.

DESCRIPTION OF EMBODIMENTS

Figure 1:
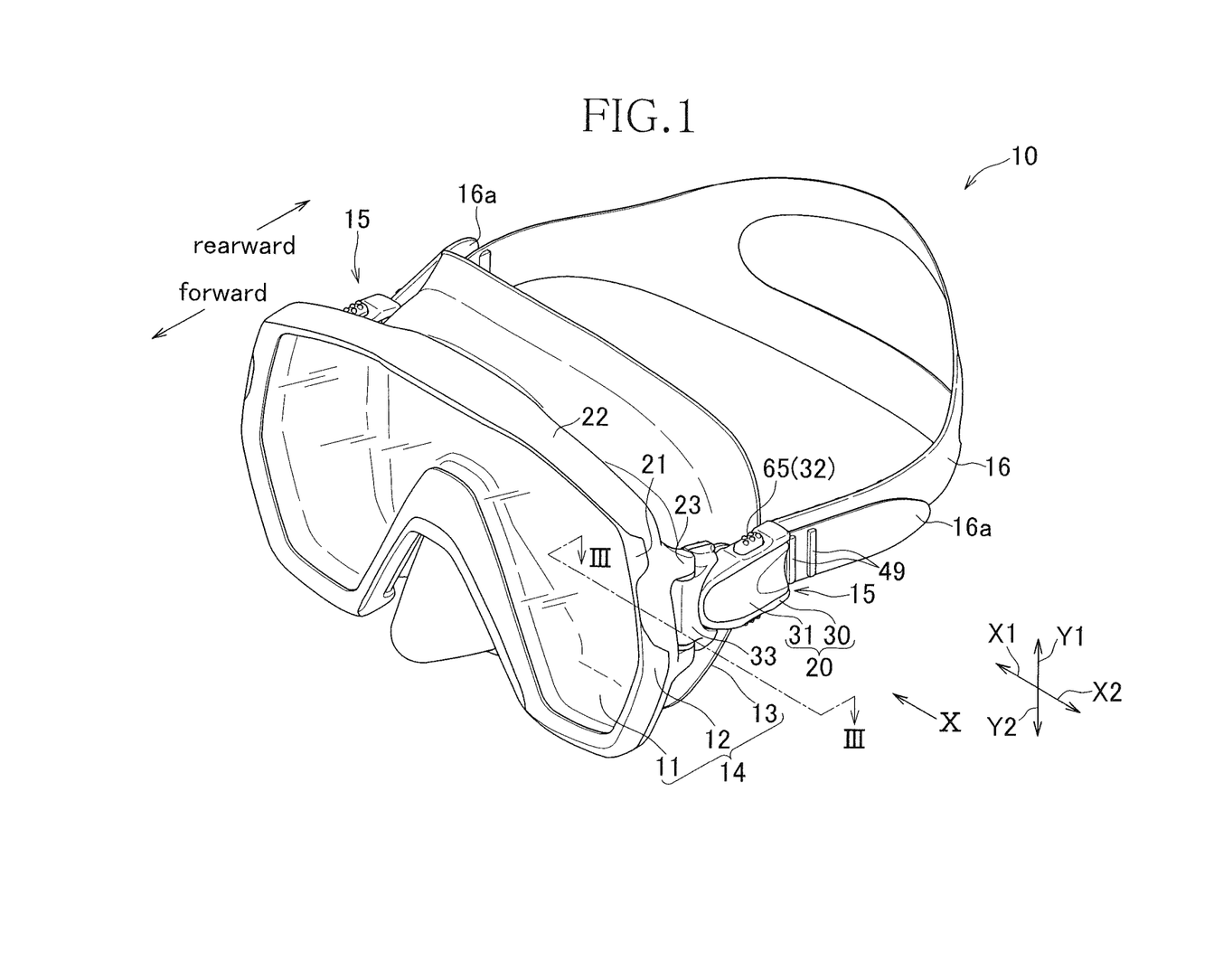
FIG. 1 is a perspective view of an underwater mask.
Figure 2:
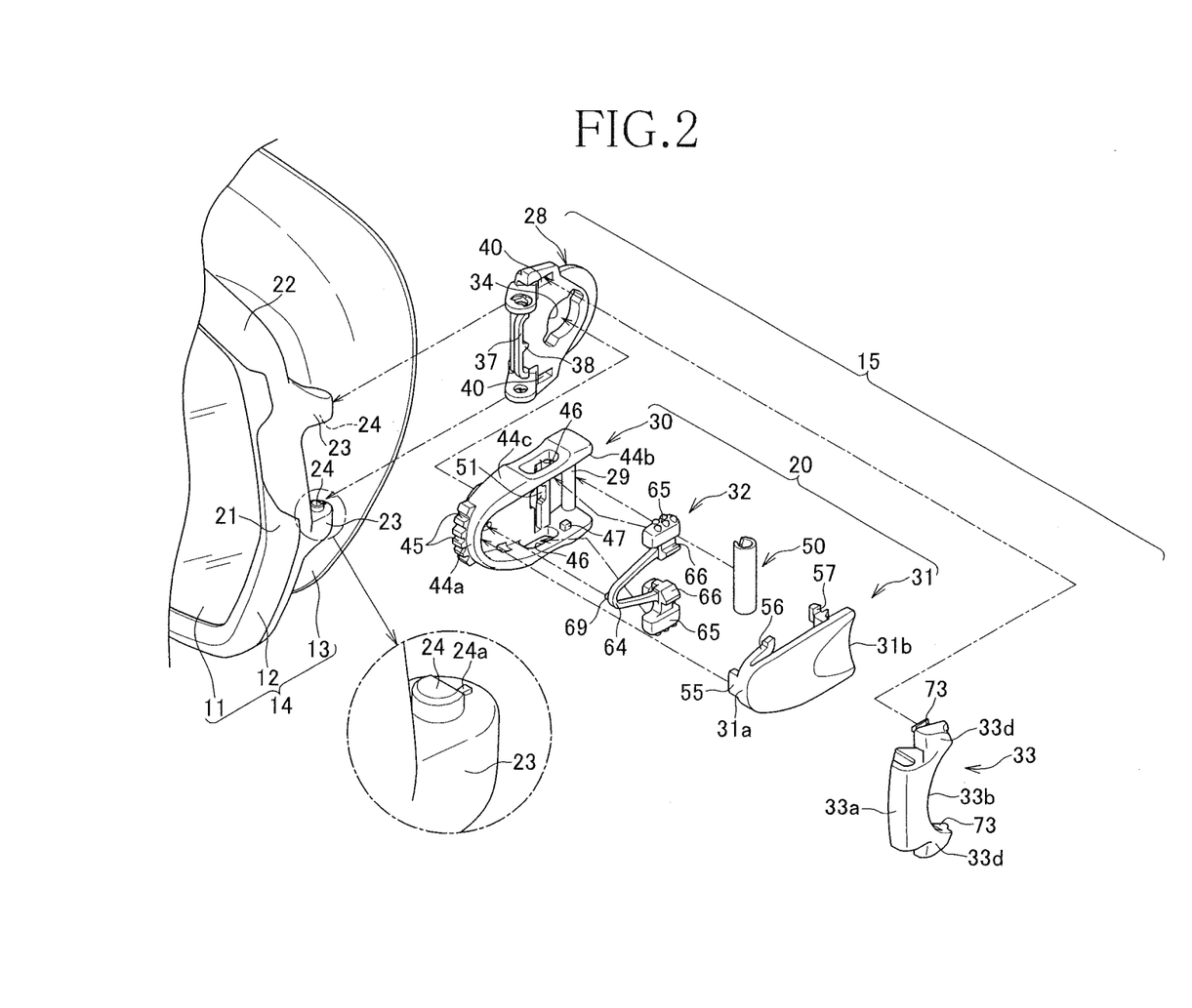
FIG. 2 is an exploded perspective view of a buckle.
Figure 3:
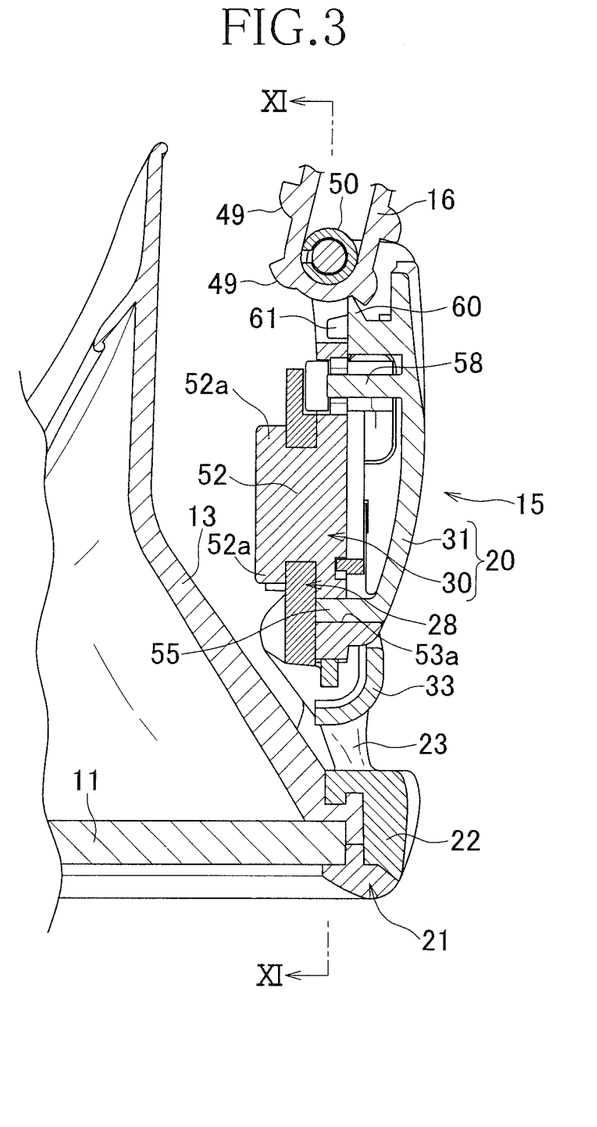
FIG. 3 is a schematic cross-sectional view along line III-III in FIG. 1.

Referring to FIGS. 1 to 3, an underwater mask 10 has up and down directions Y1 and Y2 and right and left directions X1 and X2 perpendicular to the up and down directions. The underwater mask 10 includes a mask body 14 including a lens frame 12 into which a lens 11 is fitted and a flexible skirt 13 extending rearward from the lens frame 12, and a flexible strap 16 length-adjustably wound through buckle 15 on both sides of the lens frame 12.

The lens 11 is formed of an inorganic or organic transparent plate, and the lens frame 12 is made of a rigid plastic material. The lens frame 12 includes an inner frame 21 closely contacting the outer face of the periphery of the lens 11, and an outer frame 22 closely contacting the inner face of the periphery of the inner frame 21, the frame being integrally coupled to each other. The outer frame 22 includes, on both sides of the mask body 14, a pair of coupling portions 23 on which base 28 constituting part of the buckle 15 are attached. Each of the coupling portions 23 includes a pair of arms spaced apart from each other in the up and down directions Y1 and Y2, and the inner face of the arms have short shafts 24 configured to turnably hold the base 28. On the base ends of the short shafts 24, engaging pieces 24a are disposed to which turn regulating groove 36b (see FIG. 5) described later of the base 28 are slidably fitted. Though is not shown, the coupling portions 23 may be disposed with the inner frame 21.

The buckle 15 is made of a plastic material, for example. The buckle 15 includes the base 28 coupled to the coupling portions 23 of the lens frame 12 turnably in right and left directions X1 and X2, and an adjuster unit 20. The adjuster unit 20 includes a strap adjuster body 30 held turnably in the up and down directions Y1 and Y2 with respect to the base 28 and including a guide shaft 29 for the strap 16 around which the strap 16 is length-adjustably wound, a stopper 31 attached to the strap adjuster body 30, and a handling member 32 for the stopper 31. Optionally, the buckle 15 may further include a cover 33 detachably attached to the base 28. The buckle 15 is disposed on at least one of both sides of the mask body 14.

Figure 4:
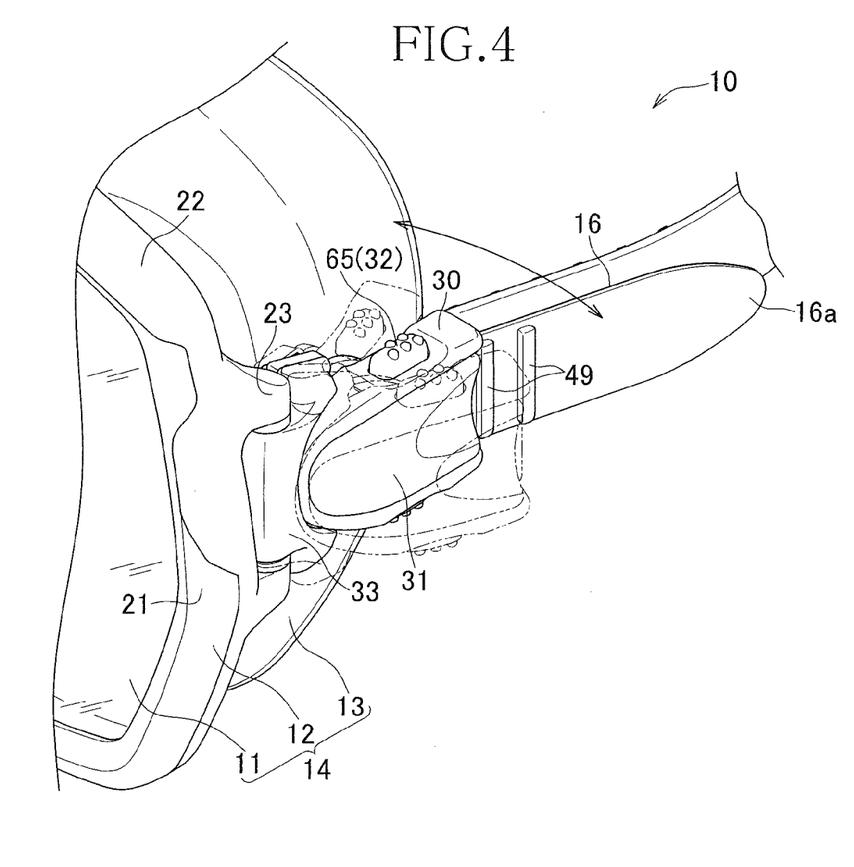
FIG. 4 is a diagram showing turn of the buckle around a coupling unit of a mask body.
Figure 5:
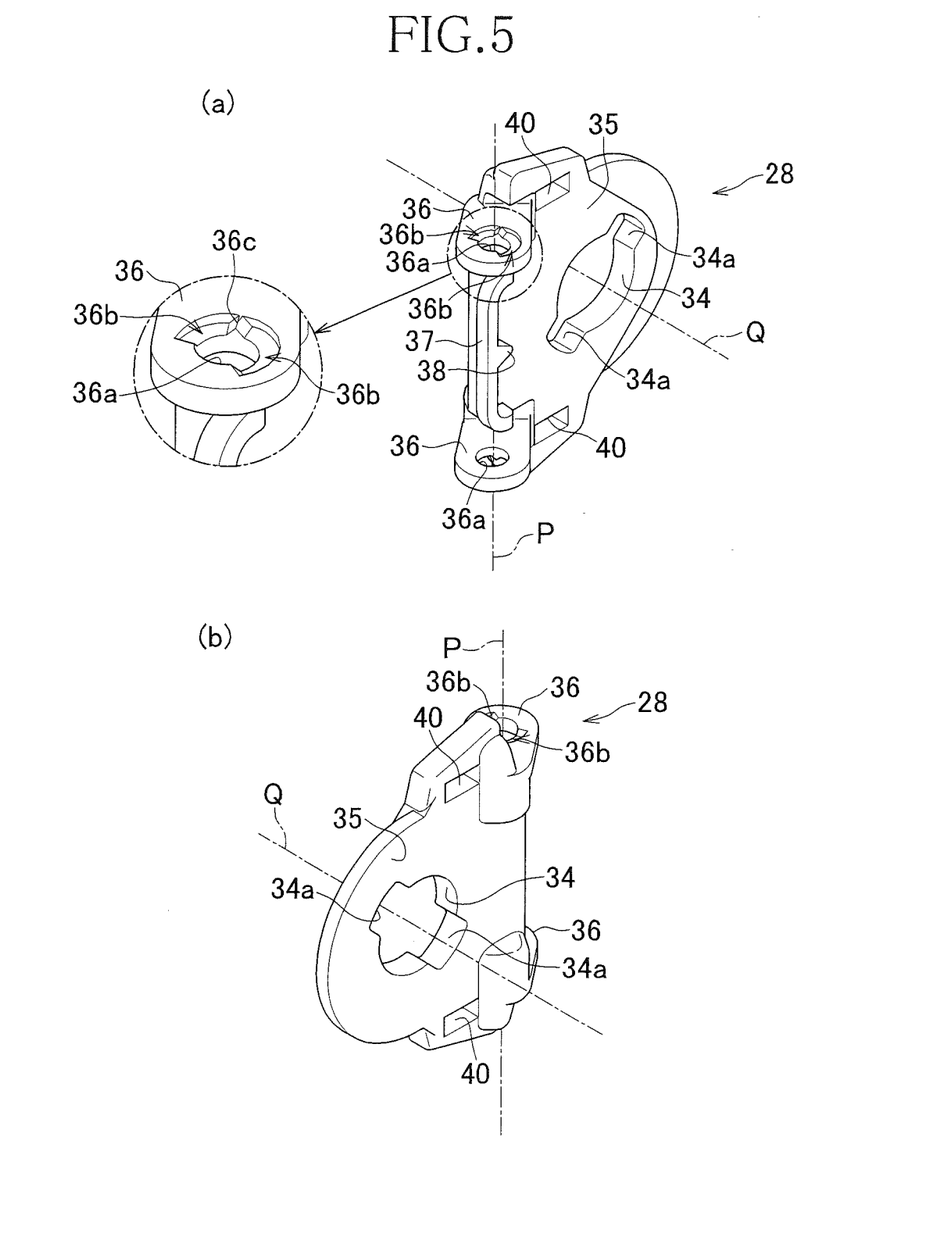
FIG. 5(a) is a front perspective view of a base.
FIG. 5(b) is a back perspective view of the base.

Referring to FIGS. 4 and 5, the base 28 includes a plate 35 (see FIG. 5(b)) having a fitting hole 34, a pair of coupling portions 36 opposed to each other in the up and down directions Y1 and Y2 on the front end, and a spring 37 extending in the up and down directions Y1 and Y2 between the coupling portions 36. The spring 37 includes a first engaging hook 38 protruding toward the plate 35. The circular fitting hole 34 includes a circular hole and a pair of guide grooves 34a opposed to each other in the radial direction of the circular hole. The coupling portions 36 each have coupling grooves 36a. The plate 35 has cover locking grooves 40 on both sides near the base ends of the coupling portions 36. The coupling portions 36 each have the arc-shaped turn regulating groove 36b on the periphery of the coupling grooves 36a, and the turn regulating groove 36b includes a protrusion 36c.

The short shafts 24 on the coupling portions 23 of the lens frame 12 are inserted into the coupling grooves 36a of the coupling portions 36, so that the base 28 is turnably held with the center of the coupling portions 23 being a pivot P. In this state, the base 28 is turnable by a predetermined angle around the pivot P because the engaging pieces 24a on the base ends of the short shafts 24 may slidably move in the turn regulating groove 36b. Accordingly, a wearer of the mask 10 can turn the buckle 15 by a predetermined angle in the right and left directions X1 and X2. Such turn angle regulation in the right and left directions X1 and X2 can adjust the position of the strap in the up and down directions Y1 and Y2 to adjust the skin fit between the mask body 14 and the wearer's face (including the forehead and a portion under the nose) in the up and down directions Y1 and Y2. In addition, moving the strap 16 in the right or left direction X1 or X2 according to the size of the wearer's face can fit the whole underwater mask 10 more closely to the wearer's head.

In such turn angle regulation, for example, abutting of the engaging pieces 24a of the coupling portions 23 and the protrusions 36c in turn regulating groove 36b gives a wearer a click feeling in order to notify the wearer of a turn range ordinarily used that is up to an angle made by turning the buckle 15 forward in the right direction X2 by a predetermined angle (about 30°) from a position orthogonal to a vertical line connecting between the coupling portions 23 extending in the up and down directions Y1 and Y2. Causing a state in which the buckle 15 is turned in the right direction X2 by more than the predetermined angle (about 30°) to be a state not ordinarily used (an irregular state) can prevent an excessive load on mask components, such as the coupling portions 23, 34, caused by turning the buckle 15 until the buckle 15 comes in contact with the lens frame 12, and can prevent breakage of part of the components. It is possible to further rotate the strap 16 in the right direction X2 by moving the engaging pieces 24a outward in the right direction X2 beyond the protrusions 36c that are disposed at a predetermined angle (about 30°) in the right direction X2. In this case, elastic deformation of the coupling portions 36 of the base 28 enables the engaging pieces 24a to climb on and pass over the engaging pieces 24a, and then the coupling portions return to the original state. The insertion of the short shafts 24 into the coupling grooves 36a is easy because of elastic deformation of the coupling portions 36 of the base 28.

Figure 6:
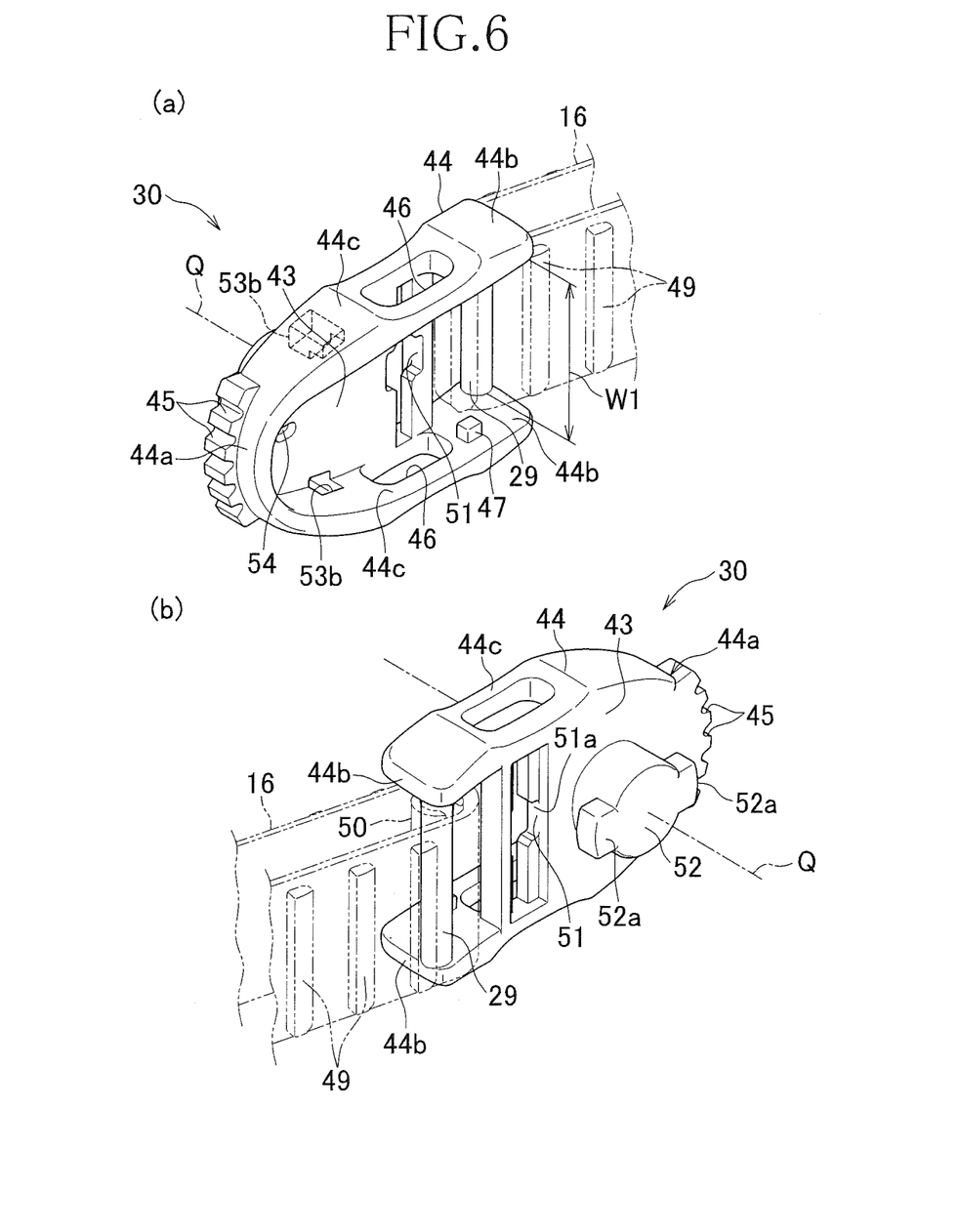
FIG. 6(a) is a front perspective view of a strap adjuster body with a strap shown by imaginary lines.
FIG. 6(b) is a back perspective view of the strap adjuster body with the strap shown by imaginary lines.

Referring to FIG. 6, the strap adjuster body 30 includes a bottom 43 and a peripheral wall 44 surrounding the bottom 43 in a U shape. The peripheral wall 44 includes front end 44a having a convex shape toward the lens frame 12, rear ends 44b, and sides 44c spaced apart from and opposite to each other in the up and down directions Y1 and Y2. The outside of the front end 44a of the peripheral wall 44 has engaging teeth 45 that are a plurality of teeth lying in line in the circumferential direction of the front end 44a. The engaging teeth 45 can sequentially engage with the engaging hook 38 of the spring 37. The sides 44c of the peripheral wall 44 each have a guide opening 46 on the rear end 44b side. The guide shaft 29 extending in the up and down directions Y1 and Y2 is disposed between the rear ends 44b. The inner face of the sides 44c each have a support protrusion 47 between the guide shaft 29 and the guide openings 46. A near-end portion 16a of the strap 16 having a plurality of approximately triangular engaging teeth 49 is wound around the guide shaft 29, and optionally a rolling shaft 50 is slidably fitted to the guide shaft 29. A portion of the bottom 43 between the guide openings 46 of the peripheral wall 44 has an approximately cross-shaped guide groove 51 extending in the up and down directions Y1 and Y2 and having wide portions 51a at the center. The bottom 43 has, near the front end 44a, a pair of protruding flanges 52a protruding from the outside of the bottom. A cylindrical fitting shaft 52 has a fitting hole 53a (see FIG. 3) on the upper front portion and has engaging depressions 53b on both sides. The cylindrical fitting shaft 52 and the protruding flanges 52a are respectively inserted into the circular fitting hole 34 and the guide grooves 34 of the base 28, and the strap adjuster body 30 is turned in the circumferential direction of the cylindrical shaft by a predetermined angle, so that the protruding flanges 52a engage with the back face of the plate 35. This engagement turnably fits the strap adjuster body 30 into the base 28 and causes the hook 38 of the spring 37 to engage with the engaging teeth 45 of the strap adjuster body 30.

Figure 8:
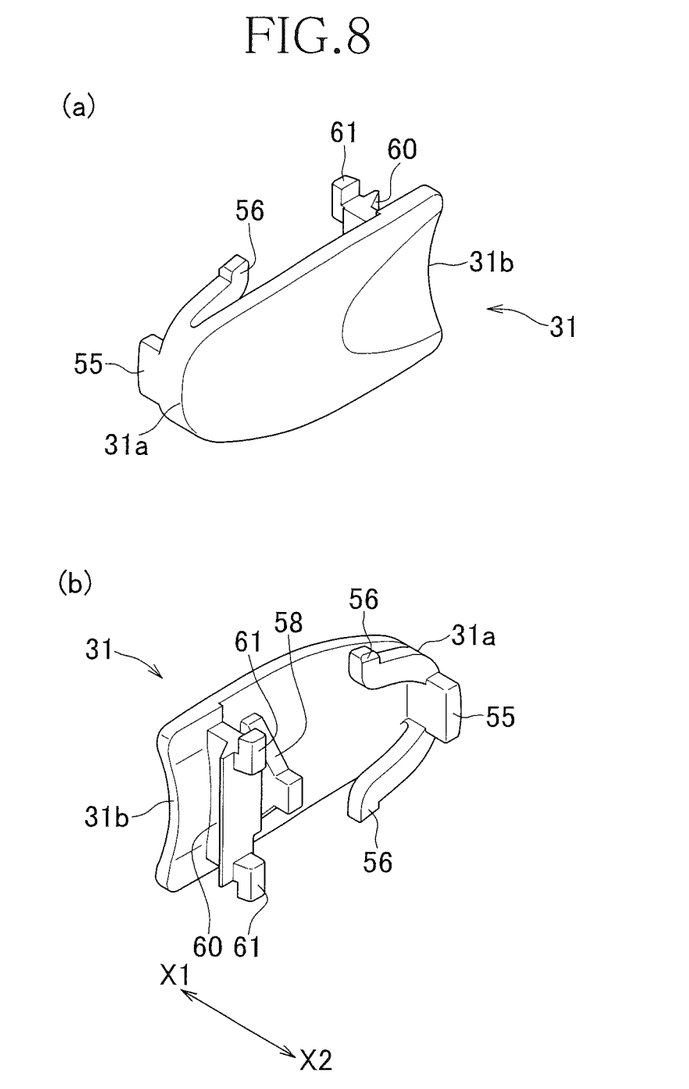
FIG. 8(a) is a front perspective view of a handling member.
FIG. 8(b) is a back perspective view of the handling member.

Referring to FIG. 8, the stopper 31 includes a convex front end 31a, a concave rear end 31b, an engaging protrusion 55 on the inner face of the front end 31a, elastic locking arms 56 extending from both sides of the engaging protrusion 55 toward the rear end 31b approximately along the side edges of the front end 31a, a pawl 60 protruding from the inner face near the rear end 31b toward a rear direction X2 and configured to sequentially engage with the engaging teeth 49 of the strap 16, an approximately triangular sliding contact tapered protrusion 58 on the inner face near the rear end 31, and a pair of locking protrusions 61 configured to prevent the stopper 31 from uselessly coming off the strap adjuster body 30.

The stopper 31 is fitted into the inside of the peripheral wall 44 of the strap adjuster body 30 as follows: the protrusion 55 engages with the fitting hole 53a (see FIG. 3) of the body; the locking arms 56 engage with the engaging depressions 53b of the body, resisting effects of the extending pressure of both side portions; the sliding contact tapered protrusion 58 is inserted into the wide portions 51a of the guide hole 51 of the body slidably in the right and left directions X1 and X2; and the locking protrusions 61 engage with the support protrusions 47 of the body from the back. Thus, the stopper 31 can swing, with the sliding contact tapered protrusion 58 being the center, along the edge of the slope of the protrusion toward the direction opposite to the strap adjuster body 30.

Figure 7:
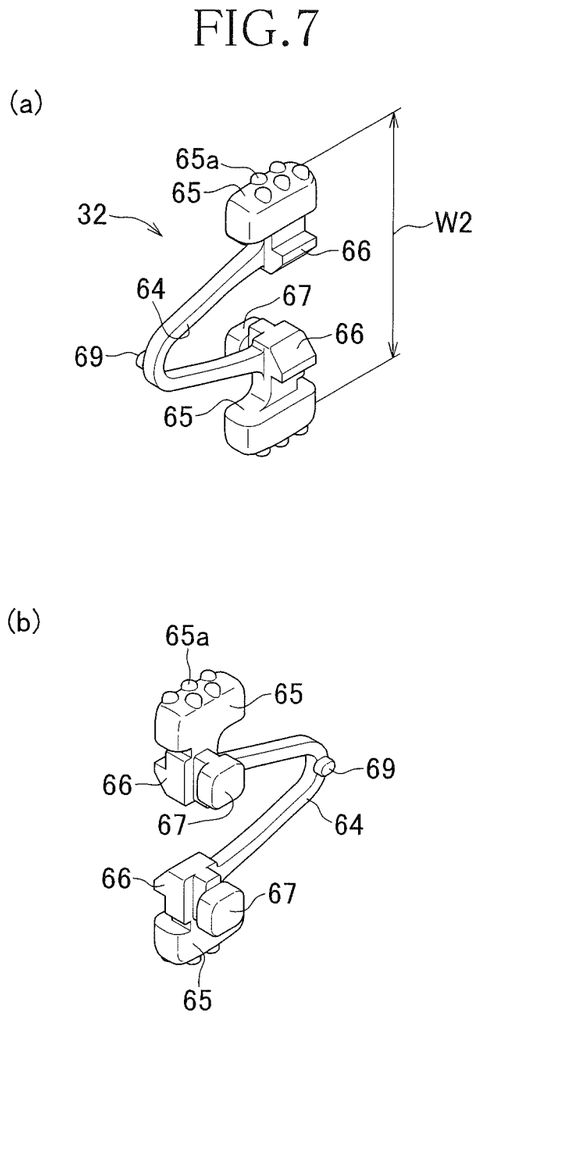
FIG. 7(a) is a front perspective view of a stopper.
FIG. 7(b) is a back perspective view of the stopper.

Referring to FIG. 7, the handling member 32 includes an approximately V-shaped spring 64 and finger pads 65 on both ends of the spring 64. The finger pads 65 each have a plurality of anti-slip protrusions 65a on the outside. The base ends of the finger pads 65 have a pair of sliding portions 66 and a pair of sliders 67 protruding from the side opposite to the sliding portion 66. The front end of the spring 64 has a protrusion 69. The handling member 32 is housed between the peripheral wall 44 (see FIG. 6) of the strap adjuster body 30. At this time, the finger pads 65 are inserted into the guide openings 46 from the inside toward the outside of the peripheral wall 44 of the body so that the finger pads 65 can move in the up and down directions Y1 and Y2 and will be exposed from the guide openings, and the protrusion 69 of the spring 64 engages with a depression 54 of the body. Accordingly, in the handling member 32, when a wearer of the mask presses the finger pads 65 toward the down direction Y2 with both fingers, the spring 64 resists the extending effects, and the space between both sides of the spring 64 becomes smaller with the protrusion 69, which engages with the depression 54, being the fulcrum. When the wearer stops the pressing, the finger pads 65 and the spring 64 return to the original state.

Figure 9:
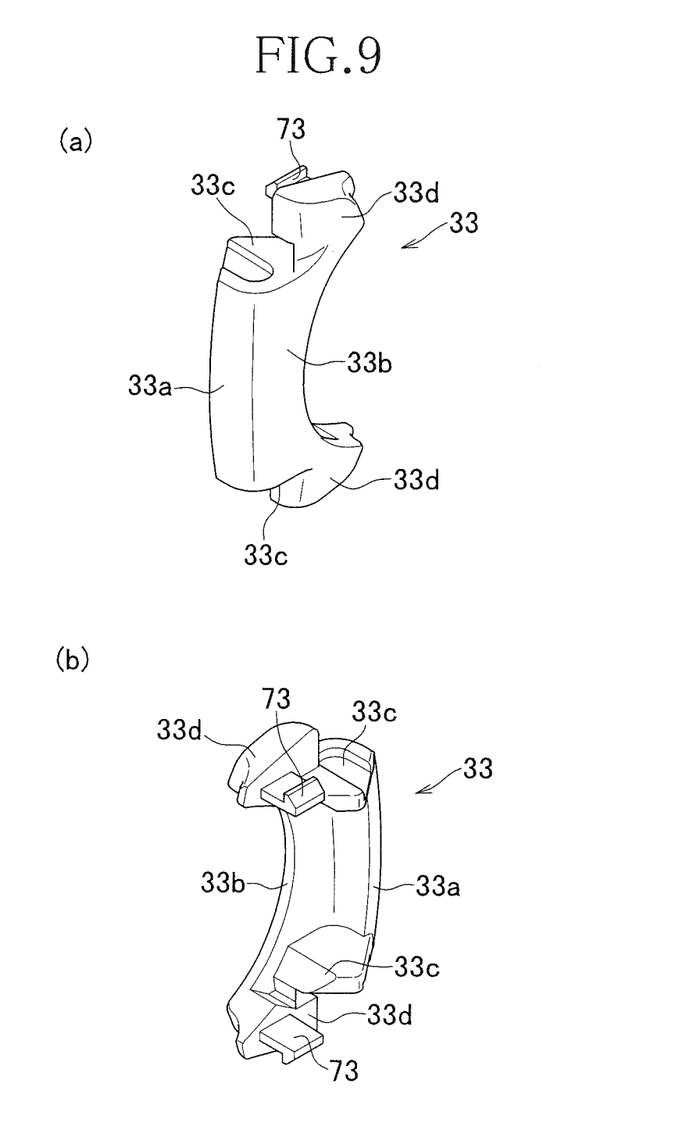
FIG. 9(a) is a front perspective view of a cover.
FIG. 9(b) is a back perspective view of the cover.

Referring to FIG. 9, the cover 33 includes an approximately linear front 33a, a single side wall 33b curved along the shape of the front end 44a of the strap adjuster body 30 (see FIG. 6), upper and lower walls 33c, and upper and lower protrusions 33d coupled to the single side wall 33b and forming steps between themselves and the upper and lower walls 33c. The inner faces of the upper and lower protrusions 33d each have a locking protrusion 73. The cover 33 is attached to the base 28 after the strap adjuster body 30 is attached to the base 28 coupled to the coupling portions 23 (see FIG. 2), the handling member 32 is disposed in the strap adjuster body 30, and the stopper 31 is attached. The attachment of the cover 33 to the base 28 is completed by locking the locking protrusions 73 with the cover locks 40 of the base 28. The front end 33a of the cover 33 abut the coupling portions 36 of the base 28, so that the front end 33a functions as stopper means for preventing the coupling portions 36 from coming off the coupling portions 23 of the lens frame 12 due to bending of the coupling portions 36 when the buckle 15 is turned.

Figure 10:
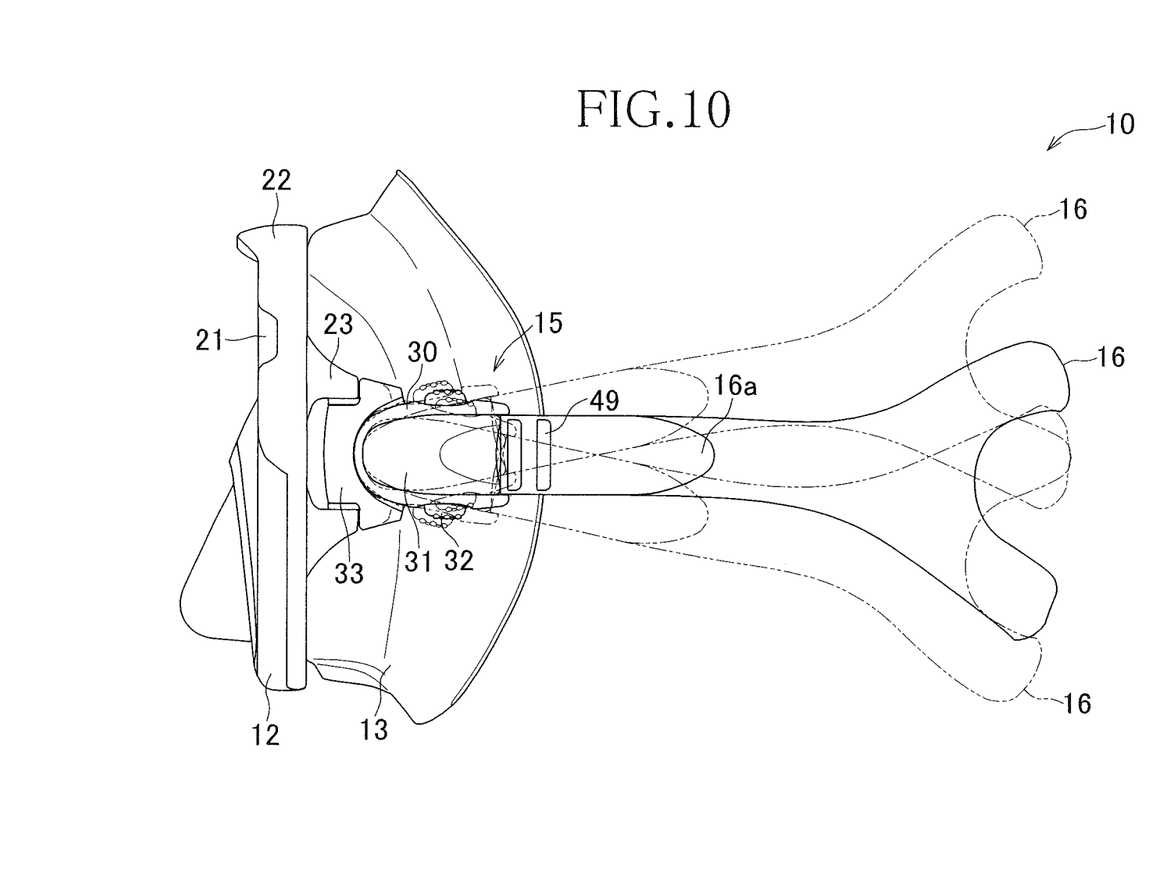
FIG. 10 is a diagram showing turn of the strap adjuster body in the longitudinal direction.
Figure 11:
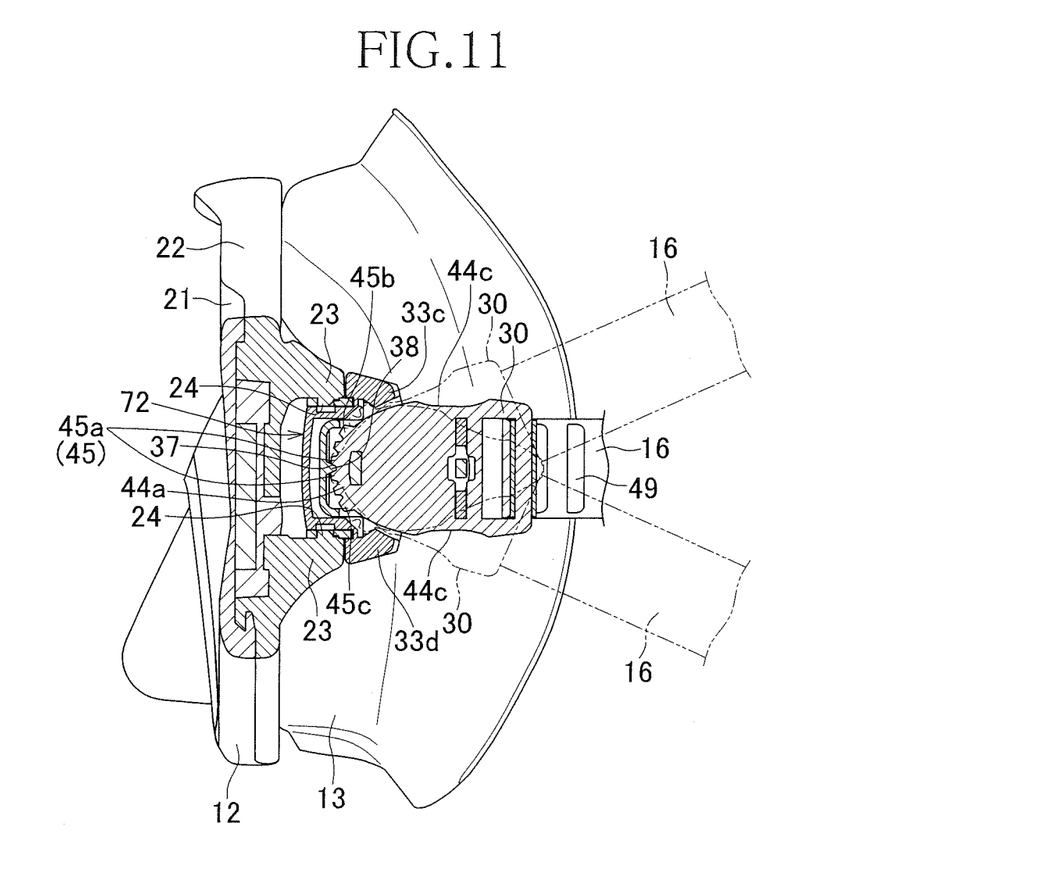
FIG. 11 is a schematic cross-sectional view along line XI-XI in FIG. 3.

Referring to FIG. 10 and FIG. 11, the strap 16 is wound around a wearer's head in an approximately horizontal direction, and central engaging teeth 45a out of the plurality of engaging teeth 45 of the strap adjuster body 30 are locked by the hook 38 of the base 28. In this state, since the strap adjuster body 30 is stably secured on the base 28, the strap adjuster body 30 does not uselessly turn even if the whole mask 10 is subjected to a relatively strong impact or the strap 16 is pulled rearward.

In the state that the strap 16 is horizontally wound around the wearer's head, when the strap adjuster body 30 is held and turned toward the up direction Y1 (or the down direction Y2), the hook 38 of the base 28 sequentially engages with from the central engaging tooth 45a to the engaging teeth 45 in the up direction (or the down direction). Accordingly, moving the strap 16 upward or downward in response to a turning operation of the strap adjuster body 30 can adjust the strap 16 to be on an appropriate position on the wearer's head. In addition, the turning operation is regulated by the plurality of engaging teeth 45 of the strap adjuster body 30, so that the strap 16 can be positioned upward or downward in a step-by-step manner.

When the strap adjuster body 30 is turned downward (or upward), the hook 38 engages with the uppermost engaging tooth 45b (or the lowermost engaging tooth 45c) and, at the same time, the strap 16 is positioned diagonally below (or diagonally above) the base 28. This state causes an upper portion (or a lower portion) of the front end 44a of the strap adjuster body 30 to come in contact with the inner face of the upper end 33c (or the lower end 33d) of the cover 33, preventing further turn.

The strap adjuster body 30 has a constitution that may further rotate even after the hook 38 passes the engaging tooth 45b or 45c. This turn of the strap adjuster body 30 is regulated by the existence of the cover 33. The protruding flanges 52a of the cylindrical fitting shaft 52 are configured not to match the guide grooves 34a of the circular fitting hole 34 while the strap adjuster body 30 is turning, so that the strap adjuster body 30 does not come off the base 28.

Referring to FIG. 4, FIG. 6, FIG. 7, and FIG. 8, when a wearer presses the finger pads 65 of the handling member 32 with, for example, the thumb and the forefinger, the sliders 67 of the handling member 32 slide along the guide groove 51 of the strap adjuster body 30, and the sliding portion 66 of the handling member, with pressure, come in contact with and slide along the edge of the slope of the sliding contact tapered protrusion 58 of the stopper 31 to cause the stopper to swing, with the protrusion 55 of the stopper 31 being the fulcrum, toward the direction opposite to the strap adjuster body 30 so as to get away from the strap adjuster body 30. This swing allows the pawl 60 of the stopper 31 to rise and release the engagement with the engaging tooth 49 of the strap 16, enabling the strap 16 to be moved and adjusted in the length direction and enabling adjustment of the fastening strength of the strap on the wearer's head. Releasing the compression of the finger pads 65 of the handling member 32 releases the pressure by the sliding portion 66 of the handling member on the edge of the slope of the sliding contact tapered protrusion 58 of the stopper 31. When the rear end of the stopper 31 is pressed in this state, the pawl 60 of the stopper engages again with an engaging tooth 49 on a corresponding position on the strap 16.

The underwater mask 10 according to the present invention is fitted on an appropriate position on a wearer's head and thus can be worn stably and contact more closely to the wearer's head than conventional buckles, which can turn only in the right and left directions X1 and X2 or the up and down directions Y1 and Y2. In addition, the underwater mask 10 is superior in portability before use, in other words, the underwater mask 10 can be carried and stored more compactly by bending the strap 16 inward using turning means.

Every constituent material of the underwater mask 10 of the present invention can be any material, such as a variety of known plastic materials, ordinarily used in this kind of field with no limitation, unless otherwise noted.

The constitution of the underwater mask according to the embodiment of the present invention described above may be arranged as below.

An underwater mask 10 has an up-down direction and a lateral direction and includes a mask body 14 and a strap 16. The mask body 14 includes a lens frame 12 and a skirt 13 extending rearward from the lens frame. The lens frame 12 includes a lens 11 on the front. The strap 16 is configured to be coupled to at least one side of both sides of the mask body through a buckle. The strap 16 includes a plurality of engaging teeth 49.

The buckle 15 includes a base 28, a strap adjuster body 30, a handling member 32, and a stopper 31. The base includes a second coupling portion 36, a fitting hole 34, and a spring 37. The second coupling portion 36 is configured to be coupled to a first coupling portion 23 on the at least one side turnably in the lateral direction. The spring 37 includes a locking hook 38. The strap adjuster body includes a plurality of engaging teeth 45, a fitting shaft 52, a guide shaft 29, a slide guide groove hole 51, and a pair of guide openings 46. The plurality of engaging teeth 45 are opposite to the spring and are capable of sequentially engaging with the locking hook. The fitting shaft 52 is configured to be fitted into the fitting hole turnably by a predetermined angle in the circumferential direction of the fitting shaft. The guide shaft 29 is configured to be wound by the strap. The slide guide groove hole 51 extends in the up-down direction. The pair of guide openings 46 is opposite to each other in the up-down direction. The handling member includes an approximately V-shaped spring 64, a slider 67, a pair of sliding portion 66 near the slider, and a pair of finger pads 65 outside the pair of sliding portion. The slider 67 is capable of sliding along the slide guide groove. The finger pads 65 are configured to be exposed from the guide openings of the strap adjuster body. The stopper includes a pawl and a sliding contact tapered protrusion 58 near the pawl. The pawl is capable of sequentially engaging with the engaging teeth of the strap. The sliding contact tapered protrusion 58 is slidably disposed between the pair of sliding portion. The stopper is configured to be held by the strap adjuster body swingably toward a direction opposite to the body.

The embodiments of the present invention may include at least the features below, which may be taken in isolation from or in combination with one another.

(1) The first coupling portion and the second coupling portion may each include a pair of coupling portions opposite to and spaced apart from each other in the up-down direction.

(2) The fitting hole of the base may have a guide hole extending outward from the fitting hole.

(3) The base may have at least one cover locking hole on both upper and lower sides of the base.

(4) The fitting shaft of the strap adjuster body may include a protruding flange configured to be fitted into the fitting hole of the base through the guide hole of the base to engage with the base.

(5) The strap adjuster body may have at least one of a plurality of engaging grooves, depressions, and protrusions configured to hold the handling member and the stopper. The handling member and the stopper may include an engaging protrusion capable of engaging with the at least one of engaging grooves, the depressions, and the protrusions.

(6) The handling member may include a pair of the sliders.

(7) The buckle may further include a cover configured to cover at least the spring of the base and the engaging teeth of the strap adjuster body. The cover may include at least one locking protrusion, on both sides of the cover, configured to engage with the cover locking hole.

The invention claimed is:

1. An underwater mask having an up-down direction and a lateral direction, comprising: a mask body having opposing sides and which comprises a lens frame having a lens on a front; a skirt extending rearward from the lens frame; and a strap configured to be coupled to at least one of the opposing sides of the mask body through a buckle, the strap having a plurality of engaging teeth, the buckle comprising: a base; a strap adjuster body; a handling member; and a stopper, the base comprising: a second coupling portion configured to be coupled to a first coupling portion on the at least one of the opposing sides turnably in the lateral direction; a fitting hole; and a spring comprising a locking hook, the strap adjuster body comprising: a plurality of engaging teeth opposite the spring configured to sequentially engage with the locking hook; a fitting shaft configured to be fitted into the fitting hole turnably by a predetermined angle in a circumferential direction of the fitting shaft; a guide shaft configured to be wound by the strap; a slide guide groove extending in the up-down direction; and a pair of guide openings opposite to each other in the up-down direction, the handling member comprising: an approximately V-shaped spring; a slider configured to slide along the slide guide groove; a pair of sliding portions near the slider; and a finger pad outside each sliding portion of the pair of sliding-portions, the finger pads configured to be exposed from the guide openings of the strap adjuster body, the stopper comprising: a pawl configured to sequentially engage with the engaging teeth of the strap; and a sliding contact tapered protrusion near the pawl, the sliding contact tapered protrusion slidably disposed between the pair of sliding portions, wherein the stopper is configured to be held by the strap adjuster body swingably toward a direction opposite to the body.

2. The mask according to claim 1, wherein the first coupling portion and the second coupling portion each comprise a pair of coupling portions opposite to each other and spaced apart from each other in the up-down direction.

3. The mask according to claim 1, wherein the fitting hole of the base has a guide hole extending outward from the fitting hole.

4. The mask according to claim 1, wherein the base has at least one cover locking hole on both upper and lower sides of the base.

5. The mask according to claim 1, wherein the fitting shaft of the strap adjuster body comprises a protruding flange configured to be fitted into the fitting hole of the base through the guide hole of the base to engage with the base.

6. The mask according to claim 1, wherein the strap adjuster body has at least one of a plurality of engaging grooves, depressions, and protrusions configured to hold the handling member and the stopper, and wherein the handling member and the stopper comprise an engaging protrusion configured to engage with the at least one of engaging grooves, the depressions, and the protrusions.

7. The mask according to claim 1, wherein the handling member comprises a pair of the sliders.

8. The mask according to claim 1, wherein the buckle further comprises a cover having opposing sides, configured to cover at least the spring of the base and the engaging teeth of the strap adjuster body, the cover comprising at least one locking protrusion, on both of the opposing sides of the cover, configured to engage with the cover locking hole.

* * * * *